United States Patent [19]

Wade

[11] Patent Number: 4,536,579

[45] Date of Patent: Aug. 20, 1985

[54] PYRIMIDINES SUBSTITUTED BY NITROGEN-CONTAINING HETEROCYCLIC RINGS AS INTERMEDIATES

[75] Inventor: James J. Wade, Oakdale, Minn.

[73] Assignee: Riker Laboratories, Inc., St. Paul, Minn.

[21] Appl. No.: 583,387

[22] Filed: Feb. 24, 1984

Related U.S. Application Data

[63] Continuation-in-part of Ser. No. 471,837, Mar. 3, 1983, Pat. No. 4,477,450.

[51] Int. Cl.$^3$ .................. C07D 405/04; C07D 413/04; C07D 417/04
[52] U.S. Cl. ..................................... 544/58.2; 544/60; 544/122; 544/295; 544/315; 544/317; 544/326
[58] Field of Search ............... 544/58.2, 60, 122, 295, 544/315, 317, 326

[56] References Cited

U.S. PATENT DOCUMENTS

| | | | |
|---|---|---|---|
| 3,045,015 | 7/1962 | Miller | 260/256.4 |
| 3,053,844 | 9/1962 | Miller et al. | 260/256.4 |
| 4,269,980 | 5/1981 | Hardy et al. | 544/256 |

FOREIGN PATENT DOCUMENTS

| | | |
|---|---|---|
| 1205144 | 1/1960 | France. |
| 859287 | 1/1961 | United Kingdom. |
| 898408 | 6/1962 | United Kingdom. |

OTHER PUBLICATIONS

Miller and Rose, x-Triazolopyrimidines, Part I, Synthesis as Potential Therapeutic Agents, J. Chem. Soc., 1963, 5642.
G. W. Miller et al., J. Chem. Soc., 1965, 3357.
Temple et al., J. Org. Chem., 1967, 33, 530.
D. J. Brown et al., Aust. J. Chem., 1978, 31, 2505.
D. J. Brown et al., Aust. J. Chem., 1979, 32, 1585.
W. J. Broadbent et al., J. Chem. Soc., 1965, 3369.
Shiho et al., Yakagaku Zasshi, 1956, 76, 804.

Primary Examiner—Richard I. Raymond
Attorney, Agent, or Firm—Donald M. Sell; James A. Smith; Robert W. Sprague

[57] ABSTRACT

1,2,4-Triazolo[4,3-c]pyrimidines substituted at the 5 or 7 position through a nitrogen atom which is part of a heterocyclic ring have been found to have potent bronchodilator activity and to be useful synthetic intermediates in the preparation of 1,2,4-triazolo[1,5-c]pyrimidines. Methods for inducing bronchodilation, pharmaceutical compositions, and synthetic processes and intermediates are also described.

2 Claims, No Drawings

PYRIMIDINES SUBSTITUTED BY NITROGEN-CONTAINING HETEROCYCLIC RINGS AS INTERMEDIATES

CROSS-REFERENCE TO RELATED APPLICATION

This application is a continuation-in-part of copending application Ser. No. 471,837 filed Mar. 3, 1983, now U.S. Pat. No. 4,477,450.

TECHNICAL FIELD

The present invention relates to triazolo[4,3-c]pyrimidines, and more specifically to 1,2,4-triazolo[4,3-c]pyrimidines. The pharmacological use of the compounds as bronchodilators, pharmaceutical compositions comprising the compounds, and intermediates useful for preparing the compounds ae also within the scope of the invention.

BACKGROUND OF THE INVENTION

Some 1,2,4-triazolo[4,3-c]pyrimidines are known to the art. Certain 3-amino-1,2,4-triazolo[4,3-c]pyrimidines are disclosed in the patents discussed below:

U.K. Pat. No. 859,287 discloses what were believed to be the compounds 3-amino-7-methyl-5-methylthio-1,2,4-triazolo[4,3-c]pyrimidine and 3-amino-7-chloro-5-methyl-1,2,4-triazolo[4,3-c]pyrimidine.

U.K. Pat. No. 898,408 discloses 3-amino-1,2,4-triazolo[4,3-c]pyrimidines which are substituted on the pyrimidine ring at the 5-position by an alkyl, alkylthio, or amino substituent, at the 7-position by an alkyl, halogen-substituted alkyl or halogen substituent, and at the 8-position by hydrogen or an alkyl or alkenyl substituent. These compounds are said to be bronchodilators.

The following related articles disclose the synthesis of certain 1,2,4-triazolo[4,3-c]pyrimidines as intermediates in the preparation of 1,2,4-triazolo[1,5-c]pyrimidiens and as potential bronchodilators. G. W. Miller et al., J. Chem. Soc., 1963, 5642, discloses, 1,2,4-triazolo[4,3-c]pyrimidines which are substituted at the 3-position by amino or imino substituents, and on the pyrimidine ring by alkyl substituents or alkyl and alkenyl substituents.

G. W. Miller et al., J. Chem. Soc., 1963, 3357, discloses the compound 3-hydroxy-7-methyl-5-n-propyl-1,2,4-triazolo[4,3-c]pyrimidine.

W. Broadbent et al., J. Chem. Soc., 1963, 3369, discloses the compound 3-mercapto-7-methyl-5-n-propyl-1,2,4-triazolo[4,3-c]pyrimidine.

Still other 3-amino-1,2,4-triazolo[4,3-c]pyrimidines are disclosed in the following articles and patent:

Shiho et al., Yakagaku Zasshi, 1956, 76, 804, discloses 1,2,4-triazolo[4,3-c]pyrimidines which are substituted at the 3-position by alkyl or phenyl substituents, and on the pyrimidine ring by both methyl and methoxy substituents.

Temple et al., J. Org. Chem., 1968, 33, 530, discloses the compound 8-amino-7-chloro-s-triazolo[4,3-c]pyrimidine-3(2 H)-one.

D. J. Brown et al., Aust. J. Chem., 1978, 31, 2505, discloses 1,2,4-triazolo[4,3-c]pyrimidines which are substituted at the 3-position by hydrogen or alkyl substituents, and on the pyrimidine ring by hydrogen and/or alkyl substituents.

D. J. Brown et al., Aust. J. Chem., 1979, 32, 1585, discloses 1,2,4-triazolo[4,3-c]pyrimidines which are substituted at the 3-position by hydrogen or an alkyl substituent, and on the pyrimidine ring at the 5-position by a halogen, hydrazino, methylthio or methyl substituent, and at the 7-position by a methyl substituent.

U.S. Pat. No. 4,269,980 discloses 5-, 7- and 8-(optionally substituted-phenyl)-1,2,4-triazolo[4,3-c]pyrimidines. These compounds may be substituted at the 3-position by hydrogen or an alkyl substitutent and are anxiolytic agents.

The triazolo[4,3-c]pyrimidines of the present invention differ from the prior art compounds in that the compounds of the present invention contain a heterocyclic substituent on the pyrimidine ring. The heterocyclic substituent is bonded to the pyrimidine nucleus in the 5 or 7 position through a nitrogen atom which is part of the heterocyclic group.

DETAILED DESCRIPTION OF THE INVENTION

The present invention relates to 1,2,4-triazolo[4,3-c]pyrimidines which are bronchodilators. The invention also relates to a method for inducing bronchodilation in a mammal using a 1,2,4-triazolo[4,3-c]pyrimidine of the invention, and to pharmaceutical compositions comprising an effective amount of a 1,2,4-triazolo[4,3-c]pyrimidine of the invention and a pharmaceutically acceptable carrier. The invention also relates to synthetic processes and intermediates useful for preparing the 1,2,4-triazolo[4,3-c]pyrimidines of the invention.

Specifically, the present invention relates to compounds of the formula I

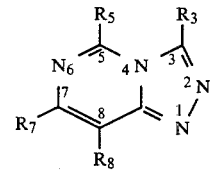

wherein R$_3$ is hydrogen or lower alkyl; one of of R$_5$ and R$_7$ is the heterocyclic substituent

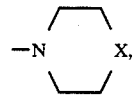

wherein X is oxygen, sulfur, sulfinyl, sulfonyl, methylene (—CH$_2$—), imido (—NH—) or N-lower alkylimido

when R$_5$ is the above heterocyclic substituent, R$_7$ is hydrogen or lower alkyl; when R$_7$ is the above heterocyclic substituent, R$_5$ is hydrogen, lower alkylthio, phenyl, or lower alkyl; and R$_8$ is hydrogen, phenyl or lower alkyl; and pharmaceutically acceptable salts thereof.

The present invention also relates to compounds of the following formula

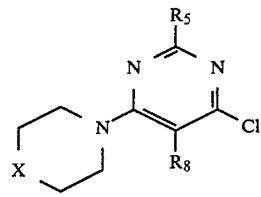

wherein R₅ is hydrogen, lower alkyl, phenyl or lower alkylthio; R₈ is hydrogen, phenyl or lower alkyl; and X is oxygen, sulfur, sulfinyl, sulfonyl, methylene, imido or N-lower alkylimido. These compounds are useful intermediates in the preparation of ciompounds of Formula I.

The present invention further relates to compounds of the following formula

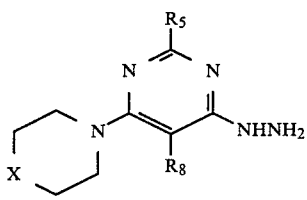

wherein R₅ is hydrogen, lower alkyl, phenyl or lower alkylthio; R₈ is hydrogen, phenyl or lower alkyl; and X is oxygen, sulfur, sulfinyl, sulfonyl, methylene, imido or N-lower alkylimido. These compounds are also useful intermediates in the preparation of compounds of Formula I.

The compounds of Formula I are also themselves useful for preparing certain 1,2,4-triazolo[1,5-c]pyrimidines which exhibit bronchodilator activity and are described in copending application U.S. Ser. No. 471,836, filed Mar. 3, 1983, and application Ser. No. 583,386, filed on the same date as the instant application, both applications being assigned to the assignee of the instant application and both being incorporated herein by reference.

"Lower alkyl" as used in the instant specification and claims designates straight or branched-chain alkyl groups containing one to about 4 carbon atoms. Preferred lower alkyl groups are methyl, ethyl and propyl.

The presently preferred compounds of Formula I are those wherein X is sulfur or oxygen and R₈ is hydrogen. These compounds are preferred because of their generally higher activity in protecting against histamine-induced contraction of isolated guinea pig tracheal tissue. This assay is discussed in greater detail below.

Specific examples of preferred compounds of Formula I which are active in the aforementioned assay at concentrations of 10 ug per ml or lower are:

3,5-bis(n-propyl)-7-(4-thiomorpholino)-1,2,4-triazolo[4,3-c]pyrimidine 5-ethyl-3-methyl-7-(4-thiomorpholino)-1,2,4-triazolo[4,3-c]pyrimidine 3-methyl-5-methylthio-8-phenyl-7-(4-thiomorpholino)-1,2,4triazolo[4,3-c]pyrimidine 5-ethyl-3-isopropyl-7-(4-thiomorpholino)-1,2,4-triazolo[4,3-c]pyrimidine 3-ethyl-5-methyl-7-(4-thiomorpholino)-1,2,4-triazolo[4,3-c]pyrimidine 3,5-bis(n-propyl)-7-(4-morpholino)-1,2,4-triazolo[4,3-c]pyrimidine 3,5-diethyl-7-(1-piperidino)-1,2,4-triazolo[4,3-c]pyrimidine 3-ethyl-7-(4-morpholino)-5-n-propyl-1,2,4-triazolo[4,3-c]pyrimidine 7-(4-morpholino)-5-methylthio-1,2,4-triazolo[4,3-c]pyrimidine 3-ethyl-5-n-propyl-7-(4-thiomorpholino)-1,2,4-triazolo[4,3-c]pyrimidine 7-(4-methyl-1-piperazino)-5-(n-propyl)-1,2,4-triazolo[4,3-c]pyrimidine 5-n-propyl-7-(4-thiomorpholino)-1,2,4-triazolo[4,3-c]pyrimidine 5-ethyl-7-(4-morpholino)-1,2,4-triazolo[4,3-c]pyrimidine 5-ethyl-3-methyl-7-(4-morpholino)-1,2,4-triazolo[4,3-c]pyrimidine 3,5-diethyl-7-(4-thiomorpholino)-1,2,4-triazolo[4,3-c]pyrimidine The bronchodilator activity of compounds of Formula I was assessed by the measurement of effects on isolated tracheal spirals. This is a well-known and conventional test method. The bronchodilator activity was determined as follows: Female guinea pigs were sacrificed and each trachea removed and cut into a spiral strip. This strip was mounted in a constant temperature (37° C.) muscle bath having a volume of approximately 15 ml. The bathing medium was Krebs-Henseleit solution. Movement of the tracheal strip was measured by means of an isometric transducer connected to an electric recorder. The bath was aerated with a mixture of 95% carbon dioxide and 5% oxygen. Contractions were induced in the strips by the addition of a suitable amount of histamine, acetylcholine or barium chloride. The amount of a given compound of Formula I (measured in microgram/ml) required to provide greater than 75% relaxation of the drug induced contraction is considered an effective concentration. For comparison, a well known standard bronchodilator, aminophylline, requires concentrations of 50 microgram/ml versus histamine, 100 microgram/ml versus acetylcholine and 10 microgram/ml versus barium chloride to provide greater than 75% relaxation.

Compounds of Formula I which were most active in the in vitro test, including most of those listed above as preferred compounds, were tested in vivo for oral activity in the guinea pig in the so-called histamine aerosol method described in U.S. Pat. No. 3,248,292. This test was modified slightly in that a 0.1% aqueous solution of histamine was used as the agent for inducing bronchial constriction. Oral doses were measured in mg/kg of body weight of the guinea pig.

Some of the compounds of the Formula I were also found to have activity as mucolytics in an in vitro test for mucus production in which rats are orally dosed with compound prior to sacrifice, and the trachea is isolated and incubated with radiolabelled glucosamine. The effect of compounds of the invention on the incorporation of glucosamine into extracellular mucus is determined. An active compound such as 5-methyl-7-thiomorpholino-1,2,4-triazolo[4,3-c]pyrimidine of the invention reduces incorporation of glucosamine.

Compounds of Formula I may be administered to mammals in order to obtain bronchodilation. The compounds may be administered orally, parenterally or by inhalation. Preferably, they are administered orally in the form of tablets or capsules. The usual effective human dose will be 0.1 to 50 mg/kg of body weight.

Salts of compounds of Formula I are generally prepared by reaction with an equimolar amount of a relatively strong acid, preferably an inorganic acid such as hydrochloric, sulfuric or phosphoric acid, in a polar solvent. Isolation of the salt is facilitated by the addition of a solvent in which the salt is insoluble, an example of such a solvent being diethyl ether.

Compounds of Formula I, either as free bases or in the form of a pharmaceutically acceptable acid-addition salt, can be combined with conventional pharmaceutical diluents and carriers to form such dosage forms as tablets, capsules, suspensions, solutions, suppositories and the like.

The pharmaceutical carrier employed may be, for example, either a solid or liquid. Examples of solid carriers are lactose, terra alba, sucrose, talc, gelatin, agar, pectin, acacia, magnesium stearate, stearic acid, and the like. Liquid carriers included syrup, peanut oil, olive oil, water and the like. Similarly, the carrier or diluent can include any time delay material well known to the art, such as glyceryl monostearate or gylceryl distearate, these being employed alone or in combination with, for example, a wax.

Compounds of Formula I may be prepared by several synthetic routes. One such route is that shown in Scheme I below. This route is useful in preparing compounds wherein $R_5$ is hydrogen, lower alkyl, lower alkylthio or phenyl; $R_7$ is

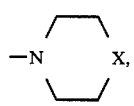

wherein X is as defined previously; and $R_3$ and $R_8$ are defined previously. Each "alk" appearing in Scheme I is independently lower alkyl.

Scheme I

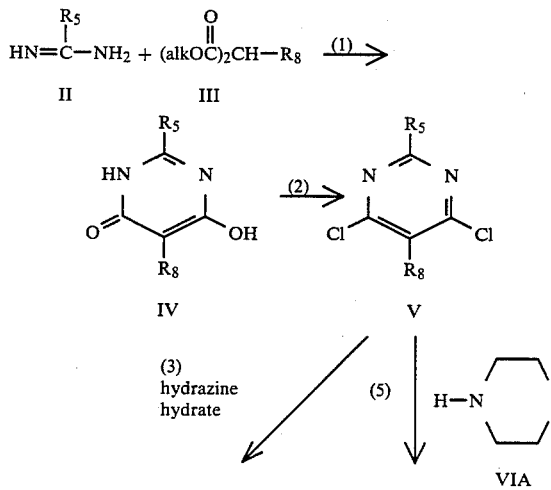

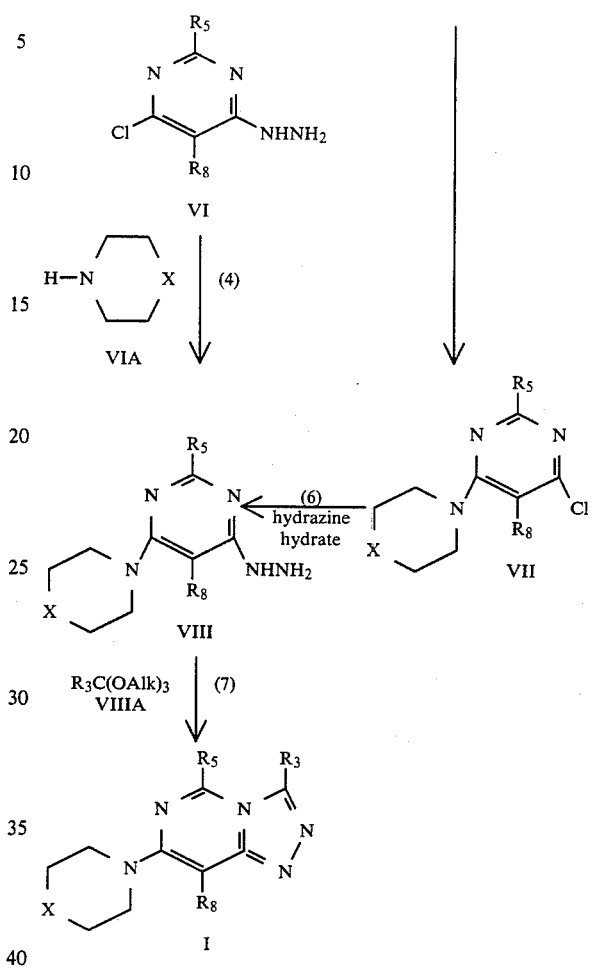

The reactions of steps (1), (2) and (3) have previously been reported for the preparation of compounds wherein $R_5$ is hydrogen, methyl or ethyl and $R_8$ is hydrogen or methyl. Thus, most of the compounds of formulas IV, V and VI are known. Heterocyclic compounds of formulas VII and VIII are novel. The known methods were used to carry out the reactions of steps (1), (2) and (3). Specifically, steps (1) and (2) were carried out as described in H. R. Henze et al., *J. Org. Chem.*, 1952, 17, 1320 and H. R. Henze et al., *J. Org. Chem.*, 1953, 18, 653, and step 3 was carried out as described in J. Chesterfield et al., *J. Chem. Soc.*, 1955, 3478. Example 1 hereinbelow details these steps.

Step (4) is carried out by reacting the optionally substituted 4-chloro-6-hydrazinopyrimidine of Formula VI with a heterocyclic amine of the formula VIA. The reactants are heated together without solvent or optionally (and preferably) in any solvent which does not participate in the reaction such as water. Two equivalents of the heterocyclic amine are preferably used. Alternatively, one equivalent of the heterocyclic amine may be replaced by an inorganic base to neutralize the hydrogen chloride, but lower yields are generally obtained. The reaction mixture is heated at a temperature up to or at its reflux temperature. A temperature is chosen which provides an adequate reaction rate. When water is used as the solvent, the temperature is generally in the range of 80° to 110° C. Good yields of the desired products are isolated by conventional methods such as filtration, extraction or chromatography. The novel intermediate of Formula VIII, which may also be prepared by steps (5) and (6) discussed below, are solids whose structural assignments are confirmed by infrared and nuclear magnetic resonance spectral analyses.

Step (5) is carried out by reacting the optionally substituted 4,6-dichloropyrimidines of Formula V with heterocyclic amines of the formula VIA. The reaction is carried out by heating the reactants without solvent or preferably in any solvent which does not participate in the reaction. Two equivalents of the heterocyclic amine are preferably used, one to react with the chloropyrimidine and the other to neutralize the hydrogen chloride by-product. Alternatively, an inorganic base can be used to neutralize the hydrogen chloride by-product, but lower yields of the desired product are generally obtained. Heating is at a temperature up to and including the reflux temperature of the mixture. A temperature is chosen which provides an adequate reaction rate. If water is used as a solvent, the mixture is generally heated at its reflux temperature. Good yields of the desired product are isolated by conventional methods such as filtration, extraction or chromatography. The novel intermediates of Formula VII are solids. Structural assignments are confirmed by infrared and nuclear magnetic resonance spectral analyses.

Step (6) is carried out by reacting the novel substituted 4-chloro-6-heterocyclicaminopyrimidine of Formula VII with hydrazine hydrate. The reaction is facile and is generally carried out at moderate temperatures, for example, from −20° C. to the reflux temperature of the solvent. The reaction is generally carried out by adding two equivalents of hydrazine hydrate to a solution of the pyrimidine. The solvent will generally be a lower alkanol. The solid product is separated by conventional methods such as filtration, extraction or chromatography and is the same novel intermediate of Formula VIII obtained from step (4).

Step (7) is carried out by reacting the intermediate of Formula VIII with an orthoester of formula VIIIA. Such orthoesters are well known and readily available. The suitable orthoesters include trimethyl orthoformate, triethyl orthoformate, triethyl orthoacetate, triethyl orthopropionate and the like. Since the orthoesters are liquids, it is convenient to mix the intermediates of Formula VIII with an excess of orthoester and to heat the mixture at reflux until reaction is complete. Good yields of the desired novel compounds of Formula I which are substituted 1,2,4-triazolo[4,3-c]pyrimidines are isolated by conventional methods. When $R_5$ is hydrogen it is necessary to monitor the reaction as it proceeds, or rearrangement to the [1,5-c] isomer may occur. Monitoring is carried out by conventional methods such as thin-layer chromatography or nuclear magnetic resonance spectral analysis. The structural assignments are made based on infrared and nuclear magnetic resonance spectral analyses. The products are generally white crystalline solids.

Heating of the compounds of Formula I in the presence of an aqueous acid as described in said application U.S. Ser. No. 471,836 provides the corresponding 1,2,4-triazolo[1,5-]pyrimidines. Alternatively, such rearrangement may be conducted in the presence of a strong base such as a metal alkoxide, for example, sodium methoxide as described in said application U.S. Ser. No. 583,386.

Scheme II shows a method for preparation of compounds of Formula I wherein $R_5$ is

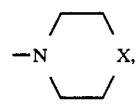

wherein X is as defined previously; $R_7$ is hydrogen or lower alkyl; and $R_3$ and $R_8$ are as defined previously.

Scheme II

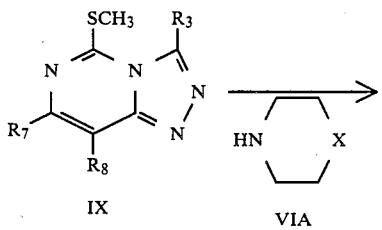

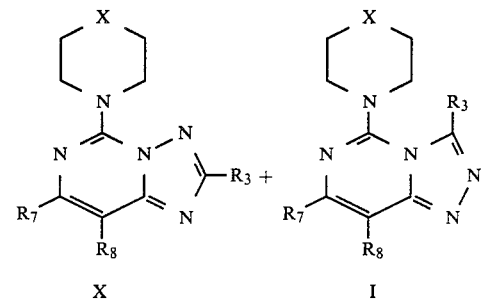

Scheme II requires heating of the intermediate of Formula IX in an excess of the heterocyclic amine of the formula VIA optionally in an inert solvent such as diglyme or dioxane. Intermediates of Formula IX are either known or may be prepared from known starting materials using known methods. The reaction is generally carried out at the reflux temperature of the mixtures. The product is isolated by conventional methods such as filtration, extraction or chromatography. Chromatography is preferred since the product is usually a mixture consisting of the desired product of Formula I and of the triazolo[1,5-c]pyrimidine of Formula X.

The following examples are provided to illustrate the methods used in the invention. They are not intended to limit the invention.

EXAMPLE 1

Preparation of 3,5-Diethyl-7-(4-methyl-1-piperazino)-1,2,4-triazolo[4,3-c]pyrimidine according to Scheme I, Steps (1), (2), (3), (4) and (7).

Part A1. Preparation of Propionamidine

Hydrogen chloride gas was bubbled into a mixture of 110 g (2.00 mole) of propionitrile and 70.0 g (2.19 mole) of methanol while cooling with an ice bath and maintaining the reaction mixture under a nitrogen stream until 78.5 g (2.15 mole) of hydrogen chloride had been added. The reaction flask was stoppered and stirred at 20° C. for 4.5 days. To this mixture was added 150 ml of methanol. Ammonia gas was bubbled into the mixture (accompanied by cooling) for two hours until the mixture was basic to litmus paper. The flask was stoppered and stirred for about 16 hours. The solids were removed by filtration, washed with methanol, and the washings and filtrate were concentrated by evaporation. The residue was dissolved in 400 ml of ethanol. The solution was cooled and then filtered, and the filtrate was concentrated by evaporation. The residue was again dissolved in ethanol, cooled, filtered and the filtrate evaporated to provide a residue which crystallized to provide 114 g (53%) of propionamidine hydrochloride.

Part A2. Alternative Preparation of Propionamidine

A mixture of 35 g (0.2 mole) of triethyl orthopropionate and 15.4 g (0.2 mole) of ammonium acetate was reacted as described by Taylor, et. al., *J. Am. Chem. Soc.*, 1960, 82, 3138, by heating the mixture at reflux for 45 minutes. The product was isolated by distilling off ethanol, followed by filtration to provide 17 g of propionamidine acetate, m.p. 165°–167° C. An additional 3 g was obtained by concentrating the filtrate and adding acetone to provide a 77% yield overall. The structure was confirmed by nuclear magnetic resonance and infrared spectral analyses.

Part B1. Preparation of 4,6-Dihydroxy-2-ethylpyrimidine according to Step (1)

To a cooled, stirred solution of 25% sodium methoxide (1200 ml, 5.55 mole) was added a slurry of 200 g (1.85 mole) of propionamidine hydrochloride in 300 ml of methanol. Next, 244 g (1.85 mole) of dimethyl malonate was added and the mixture was permitted to warm to about 20° C., after which it was stirred for 16 hours. The mixture was evaporated in vacuo and water (about 2 l) was added. This mixture was neutralized with concentrated hydrochloric acid to provide a white precipitate which was separated by filtration to provide 230 g (96%) of 4,6-dihydroxy-2-ethylpyrimidine, m.p. 312°–215° C. The structural assignment was confirmed by infrared and nuclear magnetic resonance spectral analyses.

Part. B2. Alternative Preparation of 4,6-Dihydroxy-2-ethylpyrimidine

Using the procedure of Example 1, Part B1, 18.5 g (0.14 mole) of propionamidine acetate and 90 ml of 25% sodium methoxide were reacted with dimethyl malonate (0.14 mole) to provide 16.5 g (89.5%) of 4,6-dihydroxy-2ethylpyrimidine according to Step (1).

Part C. Preparation of 4,6-Dichloro-2-ethylpyrimidine

A mixture of 150 g (1.15 mole) of 4,6-dihydroxyl-2-ethylpyrimidine and 1073 g (7.0 mole, 640 ml) of phosphorus oxychloride was heated at reflux for 6 hours, cooled and evaporated in vacuo to provide a brown oil as the residue. The residue was poured into 1500 ml of an ice-water mixture. The mixture was extracted thrice with 400 ml portions of diethyl ether. The combined ether extracts were washed sequentially with water (200 ml), 5% sodium hydroxide solution (twice with 200 ml portions), and saturated sodium chloride solution (200 ml), and were then dried over magnesium sulfate. Evaporation of the ether provided an oil which was distilled to provide 41 g (70%) of 4,6-dichloro-2-ethylpyrimidine, b.p. 55–60 C/1.5 to 4 mm Hg. The structural assignment was confirmed by infrared and nuclear magnetic resonance spectral analyses.

Part D. Preparation of 4-Chloro-2-ethyl-6-hydrazinylpyrimidine according to Step (3)

To a stirred, cold (0° C.) solution of 60 g (0.34 mole) of 4,6-dichloro-2-ethylpyrimidine in 500 ml of methanol was added 35 g (0.7 mole) of hydrazine hydrate while maintaining the temperature below 10° C. Stirring was continued for 2 hours after completion of the addition, the temperature being maintained at 0° C. The mixture was allowed to warm to about 20° C. and was stirred for 16 hours. The white solid was collected by filtration and the filtrate was partially evaporated to provide a second crop. The combined solids were washed with water and air dried to provide 51 g (77%) of 4-chloro-2-ethyl-6-hydrazinylpyrimidine, m.p. 147°–150° C.

Part E. Preparation of 2-Ethyl-6-hydrazinyl-4-(4-methyl-1-piperazinyl)pyrimidine according to Step (4)

A mixture of 8.3 g (0.05 mole) of 4-chloro-2-ethyl-6-hydrazinylpyrimidine and 11 g (0.10 mole) of 1-methyl-piperazine in 250 ml of water was heated at reflux for 16 hours and was then cooled and extracted with chloroform. The extracts were dried over magnesium sulfate and were then evaporated to provide 8.3 g (70%) of 2-ethyl-6-hydrazinyl-4-(4-methyl-1-piperazinyl)pyrimidine.

Part F. Preparation of 3,5-Diethyl-7-(4-methyl-1-piperazinyl)-1,2,4-triazolo[4,3-c]pyrimidine according to Step (7)

A mixture of 8.3 g (0.035 mole) of 2-ethyl-6-hydrazinyl-4-(4-methyl-1-piperazinyl)pyrimidine and 75 ml of triethyl orthopropionate was heated at reflux for 48 hours. After cooling the mixture was evaporated in vacuo. Diethyl ether was added to the residue and the mixture was cooled. The precipitate was collected by filtration to provide 4.5 g (37%) of 3,5-diethyl-7-(4-methyl-1-piperazinyl)-1,2,4-triazolo[4,3-c]pyrimidine. Recrystallizations from ethyl acetate-hexane and ethyl acetate-cyclohexane provided white crystalline product, m.p. 128°–131° C. Analysis for $C_{14}H_{22}N_6$: Calculated: %C, 61.3; %H, 8.1; %N, 30.6; Found: %C, 59.8; %H, 8.2; %N, 30.1. The structural assignment was confirmed by nuclear magnetic resonance and infrared spectral analyses.

EXAMPLES 2–23

Using the method of Example 1, Part E, the indicated amines of Formula VIA were reacted with the indicated known 4-chloro-2-alkyl-6-hydrazinylpyrimidines of Formula VI to provide the novel intermediates of Formula VIII (Table I).

TABLE I

| Example | Amine Intermediate | Pyrimidine Intermediate of Formula VI | Intermediate of Formula VIII | Melting Point (in °C.) |
|---|---|---|---|---|
| 2 | piperidine (HN, 6-membered ring) | 2-ethyl-4-chloro-6-hydrazinopyrimidine (CH₂CH₃ at 2, Cl at 4/6, NHNH₂ at 6/4) | 2-ethyl-4-piperidino-6-hydrazinopyrimidine | none taken (yield 66%) |
| 3 | thiomorpholine (HN–S) | " | 2-ethyl-4-thiomorpholino-6-hydrazinopyrimidine | 158–160 (yield 94.5%) |
| 4 | morpholine (HN–O) | " | 2-ethyl-4-morpholino-6-hydrazinopyrimidine | 129–133 (yield 75%) |
| 5 | morpholine (HN–O) | 2-propyl-4-chloro-6-hydrazinopyrimidine ((CH₂)₂CH₃ at 2) | 2-propyl-4-morpholino-6-hydrazinopyrimidine | 112–115 |
| 6 | N-methylpiperazine (CH₃N–NH) | 2-propyl-4-chloro-6-hydrazinopyrimidine | 2-propyl-4-(4-methylpiperazin-1-yl)-6-hydrazinopyrimidine | none taken (yield 84%) |
| 7 | thiomorpholine (HN–S) | 2-propyl-4-chloro-6-hydrazinopyrimidine | 2-propyl-4-thiomorpholino-6-hydrazinopyrimidine | 144–146 (yield 71%) |
| 8 | piperidine (HN) | 2-propyl-4-chloro-6-hydrazinopyrimidine | 2-propyl-4-piperidino-6-hydrazinopyrimidine | none taken (yield 85%) |
| 9 | morpholine (HN–O) | 2-methyl-4-chloro-6-hydrazinopyrimidine (CH₃ at 2) | 2-methyl-4-morpholino-6-hydrazinopyrimidine | none taken (yield 68%) |

TABLE I-continued

| Example | Amine Intermediate | Pyrimidine Intermediate of Formula VI | Intermediate of Formula VIII | Melting Point (in °C.) |
|---|---|---|---|---|
| 10 | thiomorpholine (HN–S ring) | 6-chloro-5-methyl-2-methyl-4-hydrazino pyrimidine | 6-thiomorpholino-5-methyl-2-methyl-4-hydrazino pyrimidine | 183–185 |
| 11 | morpholine (HN–O ring) | 6-chloro-5-methyl-2-methyl-4-hydrazino pyrimidine | 6-morpholino-5-methyl-2-methyl-4-hydrazino pyrimidine | none taken (yield 66%) |
| 12 | thiomorpholine (HN–S ring) | 6-chloro-2-methyl-4-hydrazino pyrimidine | 6-thiomorpholino-2-methyl-4-hydrazino pyrimidine | 203–204 |
| 13 | N-methylpiperazine (HN–NCH$_3$ ring) | 6-chloro-2-methyl-4-hydrazino pyrimidine | 6-(4-methylpiperazin-1-yl)-2-methyl-4-hydrazino pyrimidine | 174–177 |
| 14 | morpholine (HN–O ring) | 6-chloro-4-hydrazino pyrimidine | 6-morpholino-4-hydrazino pyrimidine | 155–157 |
| 15 | thiomorpholine (HN–S ring) | 6-chloro-4-hydrazino pyrimidine | 6-thiomorpholino-4-hydrazino pyrimidine | 147–149 |
| 16 | morpholine (HN–O ring) | 6-chloro-2-isopropyl-4-hydrazino pyrimidine | 6-morpholino-2-isopropyl-4-hydrazino pyrimidine | 122–123 |
| 17 | thiomorpholine (HN–S ring) | 6-chloro-2-isopropyl-4-hydrazino pyrimidine | 6-thiomorpholino-2-isopropyl-4-hydrazino pyrimidine | 124–126 |

TABLE I-continued

| Example | Amine Intermediate | Pyrimidine Intermediate of Formula VI | Intermediate of Formula VIII | Melting Point (in °C.) |
|---|---|---|---|---|
| 18 | $CH_3N\underset{\underset{}{\diagdown\diagup}}{\diagup\diagdown}NH$ | 4-chloro-6-hydrazino pyrimidine | 4-(4-methylpiperazin-1-yl)-6-hydrazinopyrimidine | 124–126 |
| 19 | $HN\underset{\underset{}{\diagdown\diagup}}{\diagup\diagdown}O$ | 4-chloro-6-hydrazino-2-butylpyrimidine | 4-morpholino-6-hydrazino-2-butylpyrimidine | none taken |
| 20 | $HN\underset{\underset{}{\diagdown\diagup}}{\diagup\diagdown}S$ | 4-chloro-6-hydrazino-2-butylpyrimidine | 4-thiomorpholino-6-hydrazino-2-butylpyrimidine | none taken |
| 21 | $HN\underset{\underset{}{\diagdown\diagup}}{\diagup\diagdown}O$ | 4-chloro-6-hydrazino-2-isobutylpyrimidine | 4-morpholino-6-hydrazino-2-isobutylpyrimidine | (oil) |
| 22 | $HN\underset{\underset{}{\diagdown\diagup}}{\diagup\diagdown}S$ | 4-chloro-6-hydrazino-2-isobutylpyrimidine | 4-thiomorpholino-6-hydrazino-2-isobutylpyrimidine | (oil) |
| 23 | $HN\underset{\underset{}{\diagdown\diagup}}{\diagup\diagdown}O$ | 4-chloro-6-hydrazino-2-phenylpyrimidine | 4-morpholino-6-hydrazino-2-phenylpyrimidine | 140–143 |

EXAMPLES 24–67

Using the method of Part F, Example 1, the indicated intermediates of Formula VIII were reacted with the indicated trialkyl orthoesters to provide the indicated compounds of Formula I (Table II).

TABLE II

| | Intermediate of Formula VIII | | | | Product of Formula I | | | | Calculated: % C; % H; % N Found: % C; % H; % N |
|---|---|---|---|---|---|---|---|---|---|
| Ex. | $R_5$ | $R_8$ | X | Ortho Ester | $R_3$ | $R_5$ | $R_8$ | X | (m.p. in °C.) |
| 24 | $CH_3$ | H | $SO_2$ | triethyl orthoformate | H | $CH_3$ | H | $SO_2$ | 44.9; 4.9; 26.2 44.9; 4.9; 26.3 (299–300) |
| 25 | $CH_3$ | H | $SO_2$ | triethyl orthoacetate | $CH_3$ | $CH_3$ | H | $SO_2$ | 47.0; 5.4; 25.0 47.1; 5.4; 24.9 (307–308) |
| 26 | $CH_2CH_2CH_3$ | H | O | triethyl orthoformate | H | $CH_2CH_2CH_3$ | H | O | 58.3; 6.9; 28.3 58.2; 7.0; 28.4 (200–202) |

TABLE II-continued

| Ex. | Intermediate of Formula VIII | | | Ortho Ester | Product of Formula I | | | | Calculated: % C; % H; % N Found: % C; % H; % N (m.p. in °C.) |
|---|---|---|---|---|---|---|---|---|---|
| | $R_5$ | $R_8$ | X | | $R_3$ | $R_5$ | $R_8$ | X | |
| 27 | $CH_2CH_2CH_3$ | H | O | triethyl orthopropionate | $CH_2CH_3$ | $CH_2CH_2CH_3$ | H | O | 61.1; 7.7; 25.4<br>60.9; 7.9; 25.7<br>(179-181) |
| 28 | $CH_2CH_2CH_3$ | H | S | triethyl orthoformate | H | $CH_2CH_2CH_3$ | H | S | 54.7; 6.5; 26.6<br>54.6; 6.5; 26.9<br>(208-209) |
| 29 | $CH_2CH_2CH_3$ | H | S | triethyl orthopropionate | $CH_2CH_3$ | $CH_2CH_2CH_3$ | H | S | 57.7; 7.3; 24.0<br>57.7; 7.5; 24.4<br>(143-144) |
| 30 | $CH_2CH_2CH_3$ | H | $CH_2$ | triethyl orthopropionate | $CH_2CH_3$ | $CH_2CH_2CH_3$ | H | $CH_2$ | (as $H_2SO_4$ salt):<br>48.5; 6.8; 18.9<br>48.4; 7.0; 19.0<br>(190-192) |
| 31 | $CH_3$ | H | S | triethyl orthoformate | H | $CH_3$ | H | S | 51.0; 5.6; 29.8<br>51.0; 5.5; 29.6<br>(234-237) |
| 32 | $CH_2CH_3$ | H | $CH_2$ | triethyl orthopropionate | $CH_2CH_3$ | $CH_2CH_3$ | H | $CH_2$ | 64.8; 8.2; 27.0<br>65.1; 8.3; 27.2<br>(120-122) |
| 33 | $CH_2CH_3$ | H | S | triethyl orthopropionate | $CH_2CH_3$ | $CH_2CH_3$ | H | S | 56.3; 6.9; 25.2<br>56.1; 7.2; 25.5<br>(149-150) |
| 34 | $CH_2CH_3$ | H | S | triethyl orthoacetate | $CH_3$ | $CH_2CH_3$ | H | S | 54.7; 6.5; 26.6<br>54.4; 6.7; 26.7<br>(168-170) |
| 35 | $CH_2CH_3$ | H | S | triethyl orthoformate | H | $CH_2CH_3$ | H | S | 53.0; 6.0; 28.1<br>52.6; 6.2; 28.2<br>(243-245) |
| 36 | $CH_2CH_3$ | H | O | triethyl orthoacetate | $CH_3$ | $CH_2CH_3$ | H | O | 58.3; 6.9; 28.3<br>58.2; 7.0; 28.5<br>(200-203) |
| 37 | $CH_2CH_3$ | H | O | triethyl orthopropionate | $CH_2CH_3$ | $CH_2CH_3$ | H | O | 59.7; 7.3; 26.8<br>59.6; 7.4; 27.0<br>(173-174) |
| 38 | $CH_2CH_3$ | H | O | triethyl orthoformate | H | $CH_2CH_3$ | H | O | 56.6; 6.5; 30.0<br>56.6; 6.4; 30.3<br>(223-224) |
| 39 | $CH_3$ | H | O | trimethyl orthoformate | H | $CH_3$ | H | O | 54.8; 6.0; 31.9<br>54.7; 6.0; 31.4<br>(208-210) |
| 40 | $CH_3$ | H | O | triethyl orthoacetate | $CH_3$ | $CH_3$ | H | O | 56.6; 6.5; 30.0<br>56.7; 6.3; 30.3<br>(171-173) |
| 41 | $CH_3$ | H | O | triethyl orthopropionate | $CH_2CH_3$ | $CH_3$ | H | O | 58.3; 6.9; 28.3<br>57.9; 7.0; 28.3<br>(169-172) |
| 42 | $CH_3$ | H | S | triethyl orthoacetate | $CH_3$ | $CH_3$ | H | S | 53.0; 6.0; 28.1<br>53.1; 6.3; 28.3<br>(223-225) |
| 43 | $CH_3$ | H | S | triethyl orthopropionate | $CH_2CH_3$ | $CH_3$ | H | S | 54.8; 6.5; 26.6<br>54.4; 6.7; 26.8<br>(161-163) |
| 44 | $CH_3$ | $CH_3$ | S | triethyl orthoformate | H | $CH_3$ | $CH_3$ | S | 53.0; 6.0; 28.1<br>53.2; 6.3; 28.4<br>(182-184) |
| 45 | $CH_3$ | $CH_3$ | S | triethyl orthoacetate | $CH_3$ | $CH_3$ | $CH_3$ | S | 54.7; 6.5; 26.6<br>54.4; 6.6; 26.9<br>(184-185) |
| 46 | $CH_3$ | $CH_3$ | S | triethyl orthopropionate | $CH_2CH_3$ | $CH_3$ | $CH_3$ | S | 56.3; 6.9; 25.2<br>56.4; 7.1; 25.1<br>(129-130) |
| 47 | $CH_3$ | $CH_3$ | $SO_2$ | triethyl orthoformate | H | $CH_3$ | $CH_3$ | $SO_2$ | 46.9; 5.4; 24.9<br>47.0; 5.3; 25.2<br>(234-236) |
| 48 | $CH_2CH_3$ | H | S | trimethyl orthobutyrate | $CH_2CH_2CH_3$ | $CH_2CH_3$ | H | S | 57.7; 7.3; 24.0<br>57.6; 7.5; 24.2<br>(163-165) |
| 49 | $CH_2CH_3$ | H | O | trimethyl orthobutyrate | $CH_2CH_2CH_3$ | $CH_2CH_3$ | H | O | 61.1; 7.7; 25.4<br>61.0; 7.9; 25.8<br>(164-166) |
| 50 | $CH_2CH_3$ | H | O | trimethyl orthoisobutyrate | $CH(CH_3)_2$ | $CH_2CH_3$ | H | O | 61.1; 7.7; 25.4<br>61.0; 7.7; 25.3<br>(136-137) |
| 51 | $CH_2CH_3$ | H | S | trimethyl orthoisobutyrate | $CH(CH_3)_2$ | $CH_2CH_3$ | H | S | 57.7; 7.3; 24.0<br>57.8; 7.3; 24.2<br>(143-144) |
| 52 | $CH_2CH_2CH_3$ | H | S | trimethyl orthobutyrate | $CH_2CH_2CH_3$ | $CH_2CH_2CH_3$ | H | S | 59.0; 7.6; 22.9<br>59.0; 7.5; 23.1<br>(134-135) |

TABLE II-continued

| Ex. | Intermediate of Formula VIII | | | Ortho Ester | Product of Formula I | | | | Calculated: % C; % H; % N Found: % C; % H; % N (m.p. in °C.) |
|---|---|---|---|---|---|---|---|---|---|
| | $R_5$ | $R_8$ | X | | $R_3$ | $R_5$ | $R_8$ | X | |
| 53 | $CH_2CH_2CH_3$ | H | O | trimethyl orthobutyrate | $CH_2CH_2CH_3$ | $CH_2CH_2CH_3$ | H | O | 62.3; 8.0; 24.2<br>62.2; 8.1; 24.1<br>(139–140) |
| 54 | $CH_2CH_2CH_3$ | H | S | trimethyl orthoisobutyrate | $CH(CH_3)_2$ | $CH_2CH_2CH_3$ | H | S | 59.0; 7.6; 22.9<br>59.1; 7.7; 23.0<br>(134–136) |
| 55 | $CH_2CH_2CH_3$ | H | O | trimethyl orthoisobutyrate | $CH(CH_3)_2$ | $CH_2CH_2CH_3$ | H | O | 62.3; 8.0; 24.2<br>62.4; 8.1; 24.6<br>(116–117) |
| 56 | $CH(CH_3)_2$ | H | O | triethyl orthoformate | H | $CH(CH_3)_2$ | H | O | (as $H_2SO_4$ Salt):<br>41.7; 5.5; 20.3<br>41.6; 5.7; 20.6<br>(177–178) |
| 57 | $CH(CH_3)_2$ | H | O | triethyl orthopropionate | $CH_2CH_3$ | $CH(CH_3)_2$ | H | O | (as $H_2SO_4$ Salt):<br>45.0; 6.2; 18.8<br>44.9; 6.3; 19.0<br>(167–168) |
| 58 | $CH(CH_3)_2$ | H | O | trimethyl orthobutyrate | $CH_2CH_2CH_3$ | $CH(CH_3)_2$ | H | O | (as $H_2SO_4$ Salt):<br>46.5; 6.5; 18.1<br>46.2; 6.5; 18.3<br>(162–163) |
| 59 | $CH(CH_3)_2$ | H | S | triethyl orthoacetate | $CH_3$ | $CH(CH_3)_2$ | H | S | (as $H_2SO_4$ Salt):<br>41.6; 5.6; 18.7<br>41.6; 5.8; 18.8<br>(170–172) |
| 60 | $CH(CH_3)_2$ | H | S | triethyl orthopropionate | $CH_2CH_3$ | $CH(CH_3)_2$ | H | S | (as $H_2SO_4$ Salt):<br>43.2; 6.0; 18.0<br>43.1; 6.1; 18.2<br>(174–175) |
| 61 | $C_6H_5$ | H | O | triethyl orthoformate | H | $C_6H_5$ | H | O | 64.0 5.4; 24.9<br>63.8; 5.2; 24.7<br>(>280) |
| 62 | H | H | S | trimethyl orthoformate | H | H | H | S | 48.8; 5.0; 31.7<br>48.2; 4.9; 31.3<br>(177–179) |
| 63 | H | H | $NCH_3$ | trimethyl orthoformate | H | H | H | $NCH_3$ | 55.0; 6.5; 38.5<br>54.9; 6.4; 38.1<br>(167–170) |
| 64 | $CH_3$ | H | $NCH_3$ | triethyl orthoformate | H | $CH_3$ | H | $NCH_3$ | 56.9; 6.9; 36.2<br>56.8; 6.8; 36.6<br>(177–179) |
| 65 | $(CH_2)_2CH_3$ | H | $NCH_3$ | triethyl orthopropionate | $CH_2CH_3$ | $(CH_2)_2CH_3$ | H | $NCH_3$ | 62.5; 8.4; 29.1<br>61.9; 8.5; 29.3<br>(126–129) |
| 66 | H | H | S | triethyl orthopropionate | $CH_2CH_3$ | H | H | S | 53.0; 6.1; 28.1<br>53.1; 6.2; 28.1<br>(125–127) |
| 67 | $(CH_2)_2CH_3$ | H | $NCH_3$ | triethyl orthoformate | H | $(CH_2)_2CH_3$ | H | $NCH_3$ | 60.0; 7.7; 32.2<br>59.5; 7.7; 32.0<br>(162–163) |

EXAMPLE 68

Part A. Preparation of
4-Chloro-2-methyl-6-(4-morpholino)pyrimidine by Scheme I, Step (5)

A solution of 5.00 g (31.7 mmole) of 4,6-dichloro-2-methylpyrimidine and 6.00 g (68.9 mmole) of morpholine in 50 ml of water was heated on a steam cone for about 18 hours. The mixture was diluted with water and cooled. The white solid was separated by filtration, washed with water and dried to provide 4.84 g (72%) of 4-chloro-2-methyl-6-(4-morpholino)pyrimidine. The structural assignment was confirmed by infrared and nuclear magnetic resonance spectral analyses.

Part B. Preparation of
4-Hydrazino-2-methyl-6-(4-morpholino)pyrimidine by Scheme I, Step (6)

To a mixture of 4.70 g (22 mmole) of 4-chloro-2-methyl-6-(4-morpholino)pyrimidine in 50 ml of ethanol was added to 2.2 g (44 mmole) of hydrazine hydrate and the mixture was heated at its reflux temperature for 16 hours. Cooling provided a precipitate which was separated by filtration and washed with ethanol to provide 3.15 g (68%) of white solid 4-hydrazino-2-methyl-6-(4-morpholino)pyrimidine. The structural assignment of the product was confirmed by infrared and nuclear magnetic resonance spectral analyses and comparison with the same compound made in Example 9.

EXAMPLES 69–71

Using the method of Part A, Example 68, the indicated intermediate of Formula V was reacted with the indicated amine of Formula VIA to provide the indicated intermediate of Formula VII (Table III).

TABLE III

| Example Number | Intermediate of Formula V | Heterocyclic Amine of Formula VIA | Intermediate of Formula VII |
|---|---|---|---|
| 69 | 4,6-dichloropyrimidine (N=CH–N, Cl, Cl) | morpholine | 4-chloro-6-morpholino-pyrimidine, m.p. 147.5–150° C., White Solid |
| 70 | 4,6-dichloro-2,5-dimethylpyrimidine | thiomorpholine-1,1-dioxide | corresponding product, m.p. 210–220° C., White Solid |
| 71 | 4,6-dichloro-2-methylpyrimidine | thiomorpholine-1,1-dioxide | corresponding product, m.p. about 200° C. |

EXAMPLES 72–74

Using the method of Part B, Example 68, the indicated intermediate of Formula VII was reacted with hydrazine hydrate to provide the indicated intermediate of Formula VIII (Table IV).

TABLE IV

| Example | Intermediate of Formula VII | Intermediate of Formula VIII |
|---|---|---|
| 72 | Example 69 | 4-hydrazino-6-morpholino-pyrimidine, white solid |
| 73 | Example 70 | 4-hydrazino-2,5-dimethyl-6-(thiomorpholino-1,1-dioxide)pyrimidine, m.p. 232–234° C.; white solid |
| 74 | Example 71 | 4-hydrazino-2-methyl-6-(thiomorpholino-1,1-dioxide)pyrimidine, m.p. 250–253° C.; white solid |

EXAMPLES 75–78

Additional intermediates of Formula VII which may be prepared starting with intermediates of Formula V and using the method of Example 68, Part A, are described in Table V.

TABLE V

| Example No. | Intermediate of Formula III | Heterocyclic Amine of Formula VIA | Intermediate of Formula VII |
|---|---|---|---|
| 75 | 4,6-dichloro-2-ethyl-pyrimidine | thiomorpholine | 4-chloro-2-ethyl-6-(4-thiomorpholino)pyrimidine |
| 76 | 4,6-dichloro-2-(n-propyl)-pyrimidine | piperidine | 4-chloro-6-(1-piperidinyl)-2-(n-propyl)pyrimidine |

TABLE V-continued

| Example No. | Intermediate of Formula III | Heterocyclic Amine of Formula VIA | Intermediate of Formula VII |
|---|---|---|---|
| 77 | 4,6-dichloro-2,5-dimethylpyrimidine | piperazine | 4-chloro-2,5-dimethyl-6-(1-piperazinyl)pyrimidine |
| 78 | 4,6-dichloro-2-isobutylpyrimidine | N—methyl-piperazine | 4-chloro-2-isobutyl-6-(4-methyl-1-piperazinyl)-pyrimidine |

EXAMPLE 79

Preparation According to Scheme I of 5-methylthio-7-(4-morpholino)-1,2,4-triazolo[4,3-c]pyrimidine

Part A. Preparation of 4-Hydrazinyl-2-methylthio-6-(4-morpholino)pyrimidine according to Scheme I, Step (4)

To a solution of 3.0 g (15.7 mmole) of 4-chloro-6-hydrazinyl-2-methylthiopyrimidine in 50 ml of water was added 2.8 g (32.2 mmole) of morpholine, and the mixture was heated at reflux for two days. Cooling gave a precipitate which was separated by filtration, washed with water and dried to provide off-white solid 4-hydrazinyl-2-methylthio-6-(4-morpholino)pyrimidine, m.p. 134°–144° C. The structural assignment was confirmed by infrared and nuclear magnetic resonance spectral analyses.

Part B. Preparation of 5-Methylthio-7-(4-morpholino)-1,2,4-triazolo[4,3-c]pyrimidine according to Scheme I, Step (7)

A mixture of 24.75 g (103 mmole) of 4-hydrazinyl-2-methylthio-6-(4-morpholino)pyrimidine and 200 ml of triethyl orthoformate was heated at 120° C. in an open flask for 60 hours. The mixture was cooled, then diluted with 300 ml of diethyl ether. The precipitate was separated by filtration, washed with ether and dried to provide 5-methylthio-7-(4-morpholino)-1,2,4-triazolo[4,3-c]pyrimidine, m.p. 212°–213° C. after two recrystallizations from chloroform-hexane.

EXAMPLES 80–82

Using the method of Example 79, Parts A and B, the intermediates of Formula VIII and final compounds of Formula I shown in the following table were prepared from 4-chloro-6-hydrazino-2-methylthiopyrimidine and the indicated amine of Formula VIA (Table VI). The structures of the compounds of Formulas VIII and I shown in Table VI were confirmed by infrared and nuclear magnetic resonance spectral analyses.

TABLE VI

| Example Number | Amine Reactant Formula VIA | Intermediate of Formula VIII | Compound of Formula I |
|---|---|---|---|
| 80 | HN(CH2CH2)2NCH3 (N-methylpiperazine) | SCH3-pyrimidine with CH3N-piperazinyl and NHNH2 | SCH3-triazolopyrimidine with CH3N-piperazinyl |
| 81 | HN(CH2CH2)2NH (piperazine) | SCH3-pyrimidine with HN-piperazinyl and NHNH2 | SCH3-triazolopyrimidine with HN-piperazinyl |
| 82 | HN(CH2CH2)2S (thiomorpholine) | SCH3-pyrimidine with S-thiomorpholinyl and NHNH2 | SCH3-triazolopyrimidine with S-thiomorpholinyl |

EXAMPLE 83

Preparation of 7-Methyl-5-(1-piperazino)-1,2,4-triazolo[4,3-c]pyrimidine by Scheme II A mixture of 6.00 g (33.3 mmole) of 7-methyl-5-methylthio-1,2,4-triazolo[4,3-c]pyrimidine, 30.0 g (0.35 mmole) of piperazine and 250 ml of dioxane was refluxed under nitrogen for six days. The mixture was cooled and concentrated in vacuo. The residue obtained was dissolved in 150 ml of water, and the solution was extracted four times with 150 ml portions of chloroform. The extracts were washed thrice with 150 ml portions of water and twice with 150 ml portions of sodium chloride solution, and were dried over magnesium sulfate. Evaporation of the extracts provided a yellow solid which was taken up in 150 ml in chloroform, filtered and chromatographed on a high pressure liquid chromatograph, eluting with methanol-ethyl acetate (1:1). Infrared and nuclear magnetic resonance spectral analyses showed fractions 2 and 3 to contain 7-methyl-5-(1-piperazino)-1,2,4-triazolo[1,5-c]pyrimidine, m.p. 92°–95° C. Fraction 4 contained 7-methyl-5-(1-piperazinyl)-1,2,4-triazolo[4,3-c]pyrimidine, m. p. 136°–139° C. Analysis: Calculated for $C_{10}H_{14}N_6$: %C, 55.0; %H, 6.5; %N, 38.5. Found: %C, 54.5; %H, 6.4; %N, 37.9.

EXAMPLE 84

Preparation of
7-Methyl-5-(4-methyl-1-piperazino)-1,2,4-triazolo[4,3-c]pyrimidine Using the method of Example 83, 7-methyl-5-methylthio-1,2,4-triazolo-[4,3-c]pyrimidine was reacted with 4-methylpiperazine to provide a mixture of 7-methyl-5-(4-methyl-1-piperazino)-1,2,4-triazolo[4,3-c]pyrimidine, m.p. 170°–171° C. (Analysis: Calculated for $C_{11}H_{16}N_6$: %C, 56.9; %H, 6.9; %N, 36.2; Found: %C, 57.0; %H, 6.9; %N, 35.9) and 7-methyl-5-(4-methyl-1-piperazino)-1,2,4-triazolo[1,5-c]pyrimidine, m.p. 95°–98° C. These compounds were separated by high pressure liquid chromatography using 5% methanol in ethyl acetate containing a small amount of diethylamine.

EXAMPLE 85

Preparation of
7-Methyl-5-(4-morpholino)-1,2,4-triazolo[4,3-c]pyrimidine

A mixture of 6.0 g (33 mmole) of 7-methyl-5-methylthio-1,2,4-triazolo[4,3-c]pyrimidine and 15 ml of morpholino was heated at reflux for 19 hours, cooled and diluted with diethyl ether and hexane. The solid product was separated by filtration and chromatographed on florisil, eluting sequentially with benzene, 10% ethyl acetate in benzene, 50% ethyl acetate in benzene, and ethyl acetate. Early fractions were recrystallized from a benzene-hexane mixture to provide 7-methyl-5-(4-morpholino)-1,2,4-triazolo-[1,5-c]pyrimidine, m.p. 113°–114° C. Later fractions were recrystallized from an ethyl acetate-hexane mixture, accompanied with treatment with decolorizing charcoal, to provide 7-methyl-5-(4-morpholino)-1,2,4-triazolo[4,3-c]pyrimidine, m.p. 209°–210° C. Analysis: Calculated for $C_{10}H_{13}N_5O$: %C, 54.8; %H, 6.0; %N, 31.9; Found: %C, 55.1; %H, 5.9; %N, 31.8.

EXAMPLE 86

Preparation of
3-Methyl-5-methylthio-8-phenyl-7-(4-thiomorpholino)-1,2,4-triazolo-[4,3-c]pyrimidine according to Scheme I Part A. Preparation of
4-Chloro-2methylthio-5-phenyl-6-(4-thiomorpholino)-pyrimidine A mixture of 25 g (0.093 mole) of 4,6-dichloro-2-methylthio-5-phenylpyrimidine and 20 g (0.19 mole) of thiomorpholine in 100 ml of methanol was stirred for 16 hors. The solid was separated by filtration and dried to provide white crystals of crude 4-chloro-2-methylthio-5-phenyl-6-(4-thiomorpholino)pyrimidine, m.p. 110°–125° C.

Part B. Preparation of
4-Hydrazino-2-methylthio-5-phenyl-6-(4-thiomorpholino)pyrimidine A mixture of 29 g (0.086 mole) of 4-chloro-2-methylthio-5-phenyl-6-(4-thiomorpholino)pyrimidine and 10.0 g (0.2 mole) of hydrazine hydrate in 200 ml of ethanol was heated at its reflux temperature for 70 hours. The mixture was cooled and the product was separated by filtration. The product was white crystals of 4-hydrazino-2-methylthio-5-phenyl-6-(4-thiomorpholino)pyrimidine, m.p. 170°–171° C. The structure was confirmed by infrared and nuclear magnetic resonance spectral analyses.

Part C. Preparation of
3-Methyl-5-methylthio-8-phenyl-7-(4-thiomorpholino)-1,2,4-triazolo[4,3-c]pyrimidine A mixture of 4.2 g (0.012 mole) of 4-hydrazino-2-methylthio-5-phenyl-6-(4-thiomorpholino)pyrimidine and 40 ml of triethyl orthoacetate was heated at its reflux temperature for about 64 hours, and was then allowed to cool. The solid precipitate was collected by filtration, washed with hexane and dried. Recrystallization from ethyl acetate provided 3.0 g of pale green crystals of 3-methyl-5-methylthio-8-phenyl-7-(4-thiomoropholino)-1,2,4-triazolo[4,3-c]pyrimidine, m.p. 171°–172° C. This solid was dissolved in 40 ml of hot ethanol and an equimolar amount of sulfuric acid was added. The mixture was cooled and diethyl ether was added to precipitate yellow crystals of 3-methyl-5-methylthio-8-phenyl-7-(4-thiomorpholino)-1,2,4-triazolo[4,3-c]pyrimidine dihydrogen sulfate, m.p. 193°–195° C. The salt was neutralized with ammonium hydroxide to reprecipitate the free base which was again recrystallized from ethyl acetate. Analysis: Calculated for $C_{17}H_{19}N_5S_2$: %C, 57.1; %H, 5.4; %N, 19.6; Found: %C, 56.5; %H, 5.4; %N, 19.7.

EXAMPLE 87

Preparation of
3-ethyl-5-methylthio-8-phenyl-7-(4-thiomorpholino)-1,2,4-triazolo[4,3-c]pyrimidine Using the method of Example 86, part C, the intermediate of Example 86, part B, was reacted with triethyl orthopropionate to provide 3-ethyl-5-methylthio-8-phenyl-7-(4-thiomorpholino)-1,2,4-triazolo[4,3-c]pyrimidine dihyrogen sulfate, m.p. 205°–207° C. Analysis: Calculated for $C_{18}H_{21}N_5S_2 \cdot H_2SO_4$: %C, 46.0; %H, 4.9; %N, 14.9; Found: %C, 45.9; %H, 5.1; %N, 14.9. The crude free base had a melting point of 152°–155° C.

EXAMPLE 88

Preparation of
3,5-Diethyl-7-[4-(1,1-dioxothiomorpholino)]-1,2,4-triazolo[4,3-c]pyrimidine Part A. Preparation of
4-Chloro-6-[4-(1,1-dioxothiomorpholino]-2-ethylpyrimidine To a solution of 5.4 g (40 mmole) of 1,1-dioxothiomorpholine in 100 ml of water was added 3.5 g (20 mmole) of 4,6-dichloro-2-ethylpyrimidine. The mixture was heated at its reflux temperature for one day and chilled. The white solid was collected, washed with water and dried to provide 4-chloro-6-[4-(1,1-dioxothiomorpholino)]-2-ethylpyrimidine, m.p. (crude)

164°–172° C. Thin layer chromatographic analysis on silica gel eluting with 1:9 methanol:chloroform showed one component. The structural assignment was confirmed by nuclear magnetic resonance spectral analysis.

Part B. Preparation of 6-[4-(1,1-dioxothiomorpholino)]-2-ethyl-4-hydrazinylpyrimidine To a suspension of 4.6 g (17 mmole) of 4-chloro-6-[4-(1,1-dioxothiomorpholino)]-2-ethylpyrimidine in 75 ml of methanol was added 1.7 g (34 mmole) of hydrazine hydrate. The mixture was heated at its reflux temperature for 2 days. Evaporation provided a residue which was washed thoroughly with water and examined by thin layer chromatography. The residue was about two-thirds starting material. The residue was suspended in 75 ml of methanol, 1.7 g of hydrazine hydrate was added, and the mixture was heated at reflux for one week. The mixture was cooled, then evaporated to provide a residue. The residue was washed by stirring with 100 ml of water, separated by filtration, washed with water and dried to provide tan solid 6-[4-(1,1-dioxothiomorpholino)]-2-ethyl-4-hydrazinylpyrimidine, m.p. (crude) 158°–166° C. The structural assignment was confirmed by infrared and nuclear magnetic resonance spectral analyses.

Part C. Preparation of 3,5-Diethyl-7-[4-(1,1-dioxothiomorpholino)]-1,2,4-triazolo[4,3-c]pyrimidine A suspension of 1.5 g (5.5 mmole) of 6-[4-(1,1-dioxothiomorpholino)]-2-ethyl-4-hydrazinylpyrimidine in 35 ml of triethyl orthopropionate was heated at its reflux temperature for four days, then cooled at about 0° C. for about 16 hours. The solid was collected by filtration, washed with diethyl ether and dried to provide light brown solid 3,5-diethyl-7-[4-(1,1-dioxothiomorpholino)]-1,2,4-triazolo[4,3-c]pyrimidine, m.p. (crude) 193°–199° C. Thin layer chromatography on silica gel eluting with 1:9 methanol:chloroform showed one product. The structural assignment was confirmed by nuclear magnetic resonance spectral analysis.

EXAMPLE 89

Preparation of 4-Chloro-2-ethyl-6-[4-(1-oxothiomorpholino)]pyrimidine

To a solution of 7.9 g (66 mmole) of 1-oxothiomorpholine in 150 ml of water was added 5.8 g (33 mmole) of 4,6-dichloro-2-ethylpyrimidine. The mixture was heated at its reflux temperature for 29 hours, then stirred at 20° C. for 16 hours. The mixture was stirred and chilled using an ice bath, and the solid was collected by filtration. The solid was dissolved in chloroform, and the solution was washed with water, dried over magnesium sulfate, and evaporated. The residue was a white solid which was found by thin layer chromatography on silica gel eluting with 1:9 methanol:chloroform to be chiefly the desired product, 4-chloro-2-ethyl-6-[4-(1-oxothiomorpholino)]pyrimidine and some starting material. The product is separable by chromatography.

Using the method of Example 88, Parts B and C, 4-chloro-2-ethyl-6-[4-(1-oxothiomorpholino)]pyrimidine could be reacted using Scheme I to provide 3,5-diethyl-7-[4-(1-oxothiomorpholino)]-1,2,4-triazolo[4,3-c]pyrimidine.

EXAMPLE 90

Preparation of 2-Ethyl-6-hydrazinyl-4-(4-thiomorpholino)pyrimidine

A mixture of 293 g (1.7 mole) of 4-chloro-2-ethyl-6-hydrazinylpyrimidine and 361 g (3.5 mole) of thiomorpholine in 3 liters of water was heated at reflux for 48 hours and was then cooled and isolated by filtration to provide 392.6 g (96.8%) of 2-ethyl-6-hydrazinyl-4-(4-thiomorpholino)pyrimidine. Recrystallization from benzene provided white solid, m.p. 158°–160° C.

EXAMPLE 91

Preparation of 3,5-Diethyl-7-(4-thiomorpholino)-1,2,4-triazolo[4,3-c]pyrimidine according to Step (7) of Reaction Scheme I A mixture of 354 g (1.48 mole) of 2-ethyl-6-hydrazinyl-4-(4-thiomorpholino)pyrimidine and 650 g of triethyl orthopropionate was heated at reflux for 3 days, after 1 day commencing removal of ethanol continuously by distillation. After cooling the solid was separated by filtration to provide 358 g (87%) of 3,5-diethyl-7-(4-thiomorpholino)-1,2,4-triazolo[4,3-c]pyrimidine. Recrystallization from a benzene-hexane mixture had previously been found to provide a white crystalline product, m.p. 149°–150° C. Analysis for $C_{13}H_{19}N_5S$. Calculated: %C, 56.3; %H, 6.9; %N, 25.2; Found: %C, 56.1; %H, 7.2; %N, 25.5. The structural assignment was confirmed by nuclear magnetic resonance and infrared spectral analyses.

What is claimed is:

1. A compound of the formula

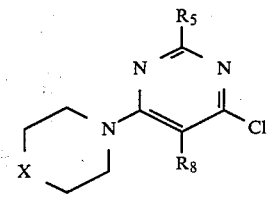

wherein $R_5$ is hydrogen, lower alkyl, phenyl or lower alkylthio; $R_8$ is hydrogen, phenyl or lower alkyl; and X is oxygen, sulfur, sulfinyl, sulfonyl, methylene, imido or N-lower alkylimido.

2. A compound of the formula

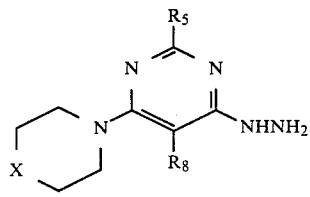

wherein $R_5$ is hydrogen, lower alkyl, phenyl or lower alkylthio; $R_8$ is hydrogen, phenyl or lower alkyl; and X is oxygen, sulfur, sulfinyl, sulfonyl, methylene, imido or N-lower alkylimido.

* * * * *